ation Data

United States Patent [19]
Lalezari

[11] Patent Number: 4,499,020
[45] Date of Patent: Feb. 12, 1985

[54] MIXED ANHYDRIDES AND PROCESSES THEREOF

[75] Inventor: Iraj Lalezari, Scarsdale, N.Y.

[73] Assignee: Montefiore Hospital and Medical Center, Inc., Bronx, N.Y.

[21] Appl. No.: 468,050

[22] Filed: Feb. 22, 1983

Related U.S. Application Data

[63] Continuation of Ser. No. 285,252, Jul. 21, 1981, abandoned.

[51] Int. Cl.$^3$ .................................................. C07J 7/00
[52] U.S. Cl. ...................................... 260/397.1; 536/6
[58] Field of Search ........................... 260/397.1; 536/6

[56] References Cited
U.S. PATENT DOCUMENTS
4,213,911  7/1980  Attwell et al. .................. 260/397.1

OTHER PUBLICATIONS

J. Org. Chem. 28 (1963) 1905–1907.
Org. Syntheses 37 pp. 20–23.
D. Nishizawa et al., "Biochemical Pharmacology" 14 pp. 1605–1619.
Fiesei et al., J.A.C.S 72 pp. 3309–3313.
Fiesei et al., J.A.C.S 73 pp. 118–122.

Primary Examiner—Elbert L. Roberts
Attorney, Agent, or Firm—Anthony J. Casella; Gerald E. Hespos

[57]     ABSTRACT

Mixed anhydrides products are described. These mixed anhydrides are produced by reaction of a carboxylic acid-containing steroid with a material having the formula:

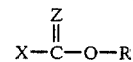

wherein:
 X is a halogen
 Z is an oxygen or sulfur
 R is a hydrocarbon in an inert organic solvent containing a Lewis base. These mixed anhydrides may in turn be reacted with, for example, an alcohol ammonia or amine to produce the corresponding ester or amide steroid.

3 Claims, No Drawings

MIXED ANHYDRIDES AND PROCESSES THEREOF

This is a continuation of application Ser. No. 285,252 filed 7-21-81, now abandoned.

BACKGROUND OF THE INVENTION

Improved means for the synthesis of organic molecules, particularly of complex molecules such as those common to biological and medicinal systems, constitutes an important part of research today. Known synthesis routes often result in only minor yields of important products and/or are totally foreclosed by the presence of interfering reactive sites present on available precursors for the products.

One important and common step in such synthesis involves the joinder of desired molecules through a carboxylic linkage unit such as an ester, amido or amide group. Representative of the molecularly complex products of this step are such important and varied compounds as:

Glycocholic acid—a clinical stimulent for bile secretion;

Taurocholic acid—a useful intermediate, the sodium salt of which is a lipase accelerator;

Ethyl cholandienate—described in U.S. Pat. No. 2,725,388;

Basic esters of bile acids—described in U.S. Pat. No. 2,562,350; and

Nucleoside esters of steroids—described in U.S. Pat. No. 4,418,059 of this inventor.

Many of these compounds cannot practically be produced by conventional techniques such as use of acyl chloride intermediates or the like. Where there exists an active site—including oxygens such as alcohol and ketone groups or an amino group—interference, instability and/or other problems arise.

There exist many other known synthesis routes for the formation of these carboxylic linkage units. One of these routes involves use of a mixed anhydride intermediate. This route is described and exemplified in the literature including the Journal of the American Chemical Society at 80, 5714; 74, 3309; 73, 118; and 72, 5530; Organic Synthesis at 37, 20; Journal of Organic Chemistry at 28, 1905 and elsewhere. The prior art, however, reflects no appreciation that these mixed anhydrides may be utilized to overcome the foregoing problems of synthesis and to facilitate the production of many important end-products.

SUMMARY OF THE INVENTION

The present invention relates to mixed anhydrides and their use and synthesis. These compounds may be formed by reacting a halo-carbonyl or halo-thiocarbonyl ester with a carboxylic acid-containing steroid. This reaction takes place in an inert organic solvent containing an organic Lewis base. This reaction is normaly exothermic. Consequently it may occur under relatively ambient temperatures.

After formation, the mixed anhydride constitutes a particularly desirable intermediate for the formation of other well-known products. Thus, for example, further reaction with an alcohol, ammonia or amine yields the corresponding ester or amide steroid.

Of particular importance, the present mixed anhydrides provide new and/or more effective means for producing valuable end-products from difficult to use starting materials. These discoveries are of special importance in the processing of complicated organic molecules such as steroids, nucleosides and the like.

Steroids having an active site such as a desirable oxygen or amine group are often very difficult to use or synthesize. Such groups are not easily masked during synthesis and consequently are often destroyed during, or interfere with, many chemical reactions. In accordance with the present invention, however, such groups are rendered innocuous. This allows ready and quantitative production of heretofore scarce and precious products.

DETAILED DESCRIPTION OF THE INVENTION

This process of the present invention involves preparing a reaction medium containing:

a. a material having the formula:

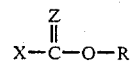

wherein:
X is a halogen;
Z is sulfur or, preferably, oxygen; and
R is a hydrocarbon;
b. a carboxylic acid-containing steroid;
c. an organic Lewis base; and
d. inert organic solvent;
and subjecting the medium to conditions effective to produce the mixed anhydride.

Incident to this reaction, the Lewis base acts primarily as an acceptor for acid halogen. While almost any such base will function, a tertiary amine such as triethyl amine is preferred. Such a strong base greatly accelerates the rate of reaction.

In the formula for the material, the hydrocarbon R with which the thiocarbonic or, preferably, carbonic acid group is esterified is relatively unimportant. It is necessary only that it block the activity of its pendant oxygen. Accordingly R may be varied broadly with little effort, although it is desirably phenyl or a lower alkyl of, for example, from 1 to 10 carbons.

The halogen of the material may also vary. Most desirably, however, it is a chloride. This halogen generally provides the optimum rate of reaction. Moreover, because of the availability of phosgene or thiophosgene as a precursor from which to produce these materials, it is particularly preferred.

To be incorporated into the present mixed anhydrides, a steroid must contain a carboxylic group. In the case of moieties natively lacking such a group, however, one may be incorporated by conventional means such as selective oxidation.

The present steroids may additionally contain an active site. By this it is meant an alcohol, ketone, amine or similarly sensitive radical. These sites will interfere with many alternative chemical synthesis agents (such as an acyl halide), but not with those of the present invention. Due to their extreme sensitivity and complicated reactivities, such active site-containing compounds represent an especially preferred class of the steroids of this invention.

The preparation of a mixed anhydride should be carried out in an inert organic solvent containing an organic Lewis base capable of facilitating their reaction. Although any such solvent may be utilized, it is desirable to employ a water miscible solvent such as dioxane. Such a solvent facilitates the performance of subsequent steps in which water may be present.

In performing the reaction, the material is desirably present in at least stoichiometric proportion to the number of carboxylic acid groups of the steroid. Preferably, this proportion is at least 1:1 by mole. The amount of Lewis base is desirably likewise at least stoichiometric. In particularly preferred embodiments, an excess of the material of up to about 50% and of Lewis base of up to 300%, more desirably from 100 to 300% is employed based on the steroid. The amount of solvent is relatively unimportant, but generally is at least equal to the total weight of the other components.

The mixed anhydrides of the present invention have the formula:

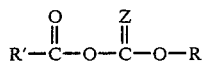

wherein: Z, R and R' are as previously described. Although these mixed anhydrides have no use per se, they are invaluable as intermediates for the production of well-known and important end-products.

Upon combination with an alcohol, for example, reaction yields an ester of the original carboxylic acid-containing steroid. This reaction is highly specific leading to a quantitative conversion.

Any alcohol may be utilized in the foregoing esterification. Indeed, the more molecularly complex the alcohol, the more apparent the advantages of use of the mixed anhydrides in the synthesis. Accordingly, alcohols having a high molecular weight constitute a preferred embodiment for the present invention. Alcohols such as sugars, starches, nucleosides and the like having a molecular weight in excess of about 70 are most preferred. Those alcohols which contain one or more ring structures, constitute a further preferred embodiment of the present invention.

Another class of desirable end-products directly producable from these mixed anhydrides are nitrogen-containing derivatives. Reaction with ammonia (or ammonium) or an amine results in the corresponding amide-steroid.

Again, the molecular complexity of the amine or end-product offers no impediment to this reaction. Quite the contrary, a preferred class of these amines includes the amino acids. These may be utilized in synthesizing very complex compounds.

The foregoing reactions may be carried out under relatively ambient conditions. If desired, elevated temperatures including reflux conditions may be employed to accelerate the rate of reaction.

The particular end-products described above are by no means the exclusive such products derivable from the present mixed anhydrides. Many others may be produced either directly or indirectly in accordance with the present invention. As may be seen from the prior discussion of such representative end-products, they amply evidence the importance of the present mixed anhydrides and the synthesis routes which they render available.

The present invention may be more fully understood by reference to the following examples which should be construed as illustrative and in no way to limit the scope of the present invention.

EXAMPLE I 0.38 ml (4 m mole) of ethyl chloro-carbonate is added dropwise to a room temperature solution of 1.57 g (4 m mole) of deoxycholic acid and 1 ml of triethylamine in 25 ml of dioxane. A precipitate of triethylammonium chloride salt is rapidly formed. After stirring for 10 minutes, the salt is filtered off and the solvent removed by evaporation under reduced pressure. The deoxycholic ethylcarbonic mixed anhydride remains as a transparent mass (yield 99%). The mixed anhydride is stable under ambient conditions for several months.

EXAMPLE II

A dioxane solution of the deoxycholic ethylcarbonic mixed anhydride produced in Example I is combined with 10 ml of concentrated ammonia. After stirring for 15 minutes, the mixture is boiled for an additional 15 minutes. The resulting white precipitate of deoxycholic amide is separated from the dioxane, washed with water and recrystallized from ethyl acetate to produce a yield of 98.7%. Composition is confirmed by melting point (sinters at 162° C.) and infrared spectra.

EXAMPLE III 1 ml of 98% hydrazine hydrate is slowly added to a solution of the mixed anhydride of Example I. After ½ hour of stirring, white precipitate is removed, washed and recrystallized from methanol at a yield of 95%. The product, deoxycholyl hydrazide, is identified by its solubility in mineral acid, melting point (211°–212° C.) and infrared spectra.

EXAMPLE IV 0.44 g of N-methyl piperazine is added to a dioxane solution of the mixed anhydride of Example I. After stirring for ½ hour, 50 ml of water is added and the solvent removed under vacuum. The resulting solid is dissolved in dilute hydrochloric acid, filtered and the free base of deoxycholyl N-methylpiperazide precipitated by neutralization with a 5% solution of sodium hydroxide. The precipitate is then recrystallized from ethyl acetate to yield (80%) a white crystalline product.

The composition of the product is confirmed by melting point (198°–200° C.) and elemental analysis based on the formula $C_{29}H_{50}N_2O_3$ as follows:

|  | C | H | N |
|---|---|---|---|
| (calculated) | 73.41 | 10.54 | 5.90 |
| (found) | 73.29 | 10.61 | 6.02 |

EXAMPLE V

The process of Example I is repeated using 1.61 g of dehydrocholic acid in place of the deoxycholic acid. After removal of the salt, 2 ml of mthanol is added to the mixed anhydride and the mixture is refluxed for ½ hour. After cooling, 50 ml of water is added to effect precipitation. Upon recrystallization from ethyl methyl ketone, 1.56 g (yield 94%) of dehydrocholyl methyl ester. The composition of the ester is confirmed by melting point (159°–161° C.) and infrared spectra.

EXAMPLE VI 10 ml of concentrated ammonia is added to a solution of dehydrocholic ethylcarbonic mixed anhydride prepared as in Example V. After stirring for 15 minutes, the mixture is boiled for an additional 15 minutes. Upon cooling, the resulting white precipitate of dehydrocholylamide is separated, washed with water and recrystallized from ethyl methyl ketone to provide a yield of 91%.

The composition of the product is confirmed by melting point (274°–275° C.) and elemental analysis based on the formula $C_{24}H_{35}NO_4$ as follows:

|  | C | H | N |
|---|---|---|---|
| (calculated) | 71.73 | 8.71 | 3.49 |
| (found) | 71.60 | 8.99 | 3.28 |

The above mentioned patents, application and other references are incorporated herein by reference. Obviously, modifications and variations of the present invention are possible in light of their and additional known teachings. It is therefore to be understood that changes may be made in the particular embodiments of the invention described which are within the full intended scope of the invention as defined by the appended claims.

What is claimed is:

1. A mixed anhydride having the formula:

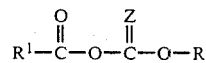

wherein Z is oxygen, $R^1$ is a residue of deoxycholic acid and R is ethyl.

2. A process for making a mixed anhydride of the formula:

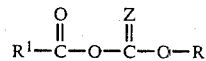

wherein Z is oxygen, $R^1$ is a residue of deoxycholic acid, and R is ethyl, said process comprising combining deoxycholic acid with ethylchlorocarbonate in the presence of an inert organic solvent and an organic Lewis base to produce a mixed anhydride of deoxycholic acid.

3. The process of claim 2 wherein the mixed anhydride is combined with 5-fluoro-2-deoxyuridine to form the ester 5-fluoro-2-deoxyuridine-di-deoxycholate.

* * * * *